United States Patent [19]

Marshall

[11] 4,421,124
[45] Dec. 20, 1983

[54] PRESSURE DETECTION ARRANGEMENT

[76] Inventor: Lee Marshall, 2808 Oregon Ct., J-3, Torrance, Calif. 90503

[21] Appl. No.: 271,794

[22] Filed: Jun. 8, 1981

Related U.S. Application Data

[62] Division of Ser. No. 51,431, Jun. 6, 1979, Pat. No. 4,286,603.

[51] Int. Cl.³ .............................................. A61B 5/10
[52] U.S. Cl. .................................... 128/782; 128/748; 128/678; 73/731; 116/268; 116/270; 137/557; 137/797
[58] Field of Search ............... 128/678, 694, 748, 782; 73/731, 146.3; 116/270, 272, 268, 34 R; 137/68 R, 797, 557

[56] References Cited

U.S. PATENT DOCUMENTS

| 618,049 | 1/1899 | Barnard et al. | 128/678 |
|---|---|---|---|
| 1,079,918 | 11/1913 | Long et al. | 137/68 R |
| 1,136,375 | 4/1915 | Smith | 137/797 |
| 1,692,360 | 11/1928 | Wolcott et al. | 73/146.3 |
| 1,900,286 | 3/1933 | Huber et al. | 128/678 |
| 2,039,337 | 5/1936 | Nolan | 128/678 |
| 2,566,369 | 9/1951 | Putman | 128/678 X |
| 2,909,927 | 10/1959 | Grant et al. | 73/731 |
| 2,989,050 | 6/1961 | Mayo et al. | 128/748 X |
| 3,604,511 | 9/1971 | Griffith et al. | 137/797 X |
| 3,625,199 | 12/1971 | Summers | 128/748 |
| 3,854,522 | 12/1974 | Didycz et al. | 137/797 |
| 3,958,562 | 5/1976 | Hakim et al. | 128/748 |
| 3,980,082 | 9/1976 | Miller | 73/731 X |
| 4,022,190 | 5/1977 | Meyer | 128/748 |
| 4,024,829 | 5/1977 | Su | 116/34 R |
| 4,155,325 | 5/1979 | Yu | 116/34 R |
| 4,172,449 | 10/1979 | Le Roy et al. | 128/748 X |
| 4,216,783 | 8/1980 | Kaiser et al. | 128/748 X |

Primary Examiner—Kyle L. Howell
Assistant Examiner—Nancy A. B. Swisher
Attorney, Agent, or Firm—Don B. Finkelstein

[57] ABSTRACT

A pressure detection arrangement embedded between the skin of a portion of the body and a means used to surround and/or immobilize that particular part of the body, such as a cast. The pressure detection arrangement is a bifurcated capsule having a reservoir cavity and an indicator cavity. A colored fluid is initially contained only within the reservoir cavity by either a frangible disc across the conjunction of the indicator cavity with the reservoir cavity or an extensible bladder within the reservoir cavity. The indicator cavity is transparent or translucent and protrudes through the cast to regions external thereto.

If there is swelling of the limb due to medical complications, the skin presses against the capsule and either breaks the frangible disc allowing the colored fluid to pass into the indicator cavity or forces the extensible bladder into the indicator cavity of the capsule. Both methods provide a visual indication in the indicator cavity of excessive pressure on the limb.

4 Claims, 13 Drawing Figures

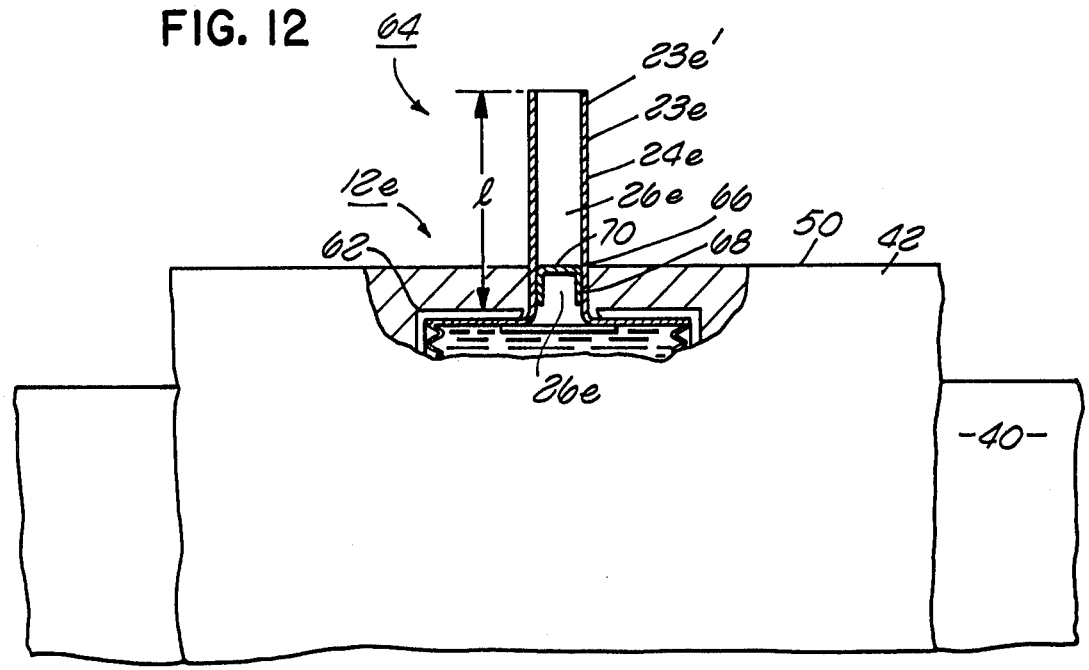
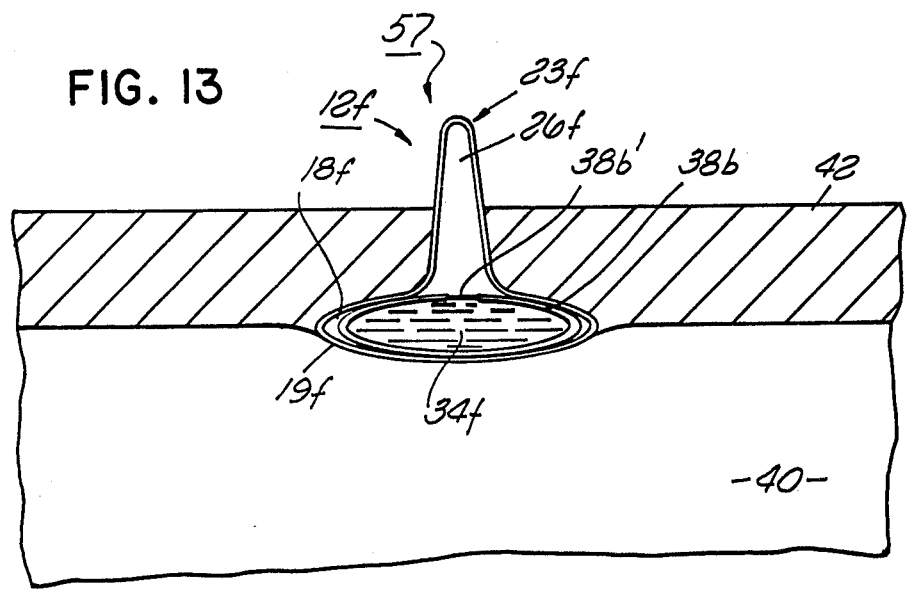

PRESSURE DETECTION ARRANGEMENT

This is a division of application Ser. No. 051,431, filed June 6, 1979, now U.S. Pat. No. 4,286,603, issued Sept. 1, 1981.

BACKGROUND OF THE INVENTION

1. Field of the Invention

This invention relates to the orthopedic medicine art and more particularly to pressure detection arrangements for indicating the pressure between limbs, or other portions of the body, and casts applied thereto.

2. Description of the Prior Art

In order to immobilize a limb, or other body portion, having a fractured bone, or for other purposes a cast is often applied to the exterior surface of the limb or body portion to hold, for example, the limb in a position which will facilitate healing of the internal bone structure. The application of an excessively tight cast or internal inflammation or swelling of the limb or body portion under the cast may cause swelling and press against the cast. Gangrene or other deleterious effects may then result from the obstruction of the blood vessels, or otherwise, due to the pressure of the cast.

In the past only the indication of swelling of the limb at the exterior end of the cast or the discomfort of the patient provided information to the physician that abnormal conditions existed within the cast. Failure to take prompt action often resulted in the loss of a limb or loss of life.

Several devices or elements of devices have been developed to detect pressure and temperature abnormalities in medical situations. U.S. Pat. No. 3,958,567 discloses a reservoir inserted between the brain and the skull attached to a tube passing through a hole in the skull for connection to a fluid pressure sensing device. A radiographic fluid is added to the system to transmit the internal pressure to the external measuring instrument. No continuous reading, independent direct pressure indication is given by the reservoir and tube alone.

U.S. Pat. No. 3,967,579 discloses a temperature sensitive device for indicating spoilage of chemical or food products after exposure for a predetermined time period to a particular predetermined temperature. As the temperature exceeds the predetermined value, a diffusion barrier permits diffusion of the temperature sensitive material onto an indicator, which causes a color change in the indicator.

U.S. Pat. No. 3,853,118 discloses two pressure sensing devices which measure the stretching of the skin, such as during an intravenous injection, by use of a conventional strain gauge or a sealed, liquid-filled capsule attached to a pressure transducer. Both require external sensing instruments.

U.S. Pat. No. 3,699,094 discloses a catheter for use with an external fluid pressure sensing device to measure intracranial pressures.

U.S. Pat. No. 3,613,679 discloses an elastic bandage which has different shaped designs imprinted thereon and the change in the size of the design while wrapping the bandage is an indication of the tension that is applied.

None of the above patents show a direct reading pressure sensitive device which may be utilized within a cast to provide a continuous, independent indication or measurement of the pressure existing between the cast and the portion of the body encased by the cast.

SUMMARY OF THE INVENTION

Accordingly, it is a primary objective of the invention to provide a pressure detection arrangement for embedding in a cast used to immobilize a particular part of the body and touching the skin of the body part for indicating to the physician by visual examination of the device at the outer surface of the cast that further medical attention is required.

It is another object of the present invention to provide an inexpensive means for detecting the pressure between a body portion encased in a cast and the rigid cast.

It is another object of the invention to diminish the number of limbs lost due to the application of casts which are too tight.

It is another object of the invention to diminish the number of limbs lost due to inflammation of the limb within a cast where swelling of the limb would otherwise lead to remedial medical attention.

These and other objects of the invention are realized in a preferred embodiment as described in detail hereinafter.

In the preferred embodiment of the present invention, there is provided a pressure detection arrangement comprised of a capsule having flexible walls defining a reservoir cavity comprised of a lower portion and an upper portion. Coupled to the top of the upper portion is an indicator means having walls defining an indicator cavity communicating with the reservoir cavity. The entire capsule is fabricated of a transparent or translucent plastic material. The indicator cavity of the capsule is separated initially from the reservoir cavity of the capsule. In one embodiment, a frangible disc is placed across the aperture between the indicator cavity and the reservoir cavity. In another embodiment, there is an extensible bladder in the reservoir cavity. In both embodiments a colored or otherwise detectable fluid is contained within the reservoir cavity under normal conditions. When, for example, a limb having a fractured bone is treated by the application of a cast to hold the bone in an immobilized position to facilitate healing, one or more pressure detection arrangements as disclosed in this invention are embedded in the cast with the lower portion of the capsule touching the skin and the indicator means protruding through the cast with at least the tip appearing on the exterior surface of the cast. When the limb swells due to inflammation or injury, the capsule is squeezed between the limb and the cast thereby exerting a pressure on the fluid within the reservoir cavity.

In the embodiment of the capsule having a frangible disc, the indicator fluid transmits the pressure to the frangible disc, and when the pressure reaches a predetermined level, the frangible disc breaks allowing the indicator fluid to pass into the indicator cavity. Because the indicator means extends to the outer surface of the cast, visual examination of the outer end of the indicator means shows the presence of fluid within the indicator cavity and thereby indicates to the observer that some abnormal condition is causing the limb to swell.

In the case of the capsule having an extensible bladder, the indicator fluid is contained within the bladder. When no pressure is exerted upon the lower portion of the capsule, the elasticity of the bladder retains the bladder within the reservoir cavity of the capsule. However, when the pressure exerted by the skin upon the capsule reaches a certain predetermined level, the upper portion of the bladder is forced into the indicator cavity.

Indicator marks can be fabricated on the portion of the indicator means extending above the exterior surface of the cast to provide a means for measuring the pressure of the limb against the interior surface of the cast. Observation of the extensible bladder used within the indicator cavity of the capsule may thus be used to monitor the effect of various medical treatments on the limb without the necessity of removing the cast. As the swelling decreases within the cast, the extensible bladder will fall. When the swelling has been reduced to normal levels, the bladder will revert to its original position within the reservoir cavity.

Several alternative embodiments of the present invention provide additional advantages. If the end of the indicator cavity at the outer surface of the cast is left open and the means for separating the indicator fluid from the indicator cavity is a frangible disc, the indicator fluid will fall entirely out of the capsule when the disc is ruptured and cause a mark on the exterior surface of the cast as well as on whatever other clothing or bedding material is adjacent to the cast. The spread of the fluid provides a positive and permanent record of the fact that excessive pressure have been produced within the cast and that further medical attention is required.

In the case of the capsule having an extensible bladder with an indicator cavity having an open upper end, the open end facilitates the movement of the extensible bladder into the indicator cavity of the capsule. Also, if the walls of the indicator cavity are trimmed flush with the exterior surface of the cast, the appearance of the extensible bladder protruding out of the cast will be more noticeable to the patient than would be the appearance of the extensible bladder within an enclosed indicator cavity. In addition, the trimming of the indicator cavity flush with the exterior of the cast eliminates the possibility of damaging the capsule by the rolling of the cast onto an object thereby applying force to the outer end of the indicator cavity.

The use of a radiographic fluid as the indicator fluid allows the monitoring by X-rays of the position of the capsule within the cast in relation to the skin.

BRIEF DESCRIPTION OF THE DRAWING

The above and other embodiments of the present invention may be more fully understood from the following detailed description taken together with the accompanying detailed drawings wherein similar reference characters refer to similar elements throughout and in which:

FIG. 12 is a sectional view similar to FIG. 10, of another embodiment of the present invention, showing the indicator cavity of the capsule trimmed flush with the outer surface of the cast and a transparent cap inserted into the indicator cavity; and FIG. 13 illustrates another embodiment of the present invention.

DESCRIPTION OF THE PREFERRED EMBODIMENTS

Figure 1:
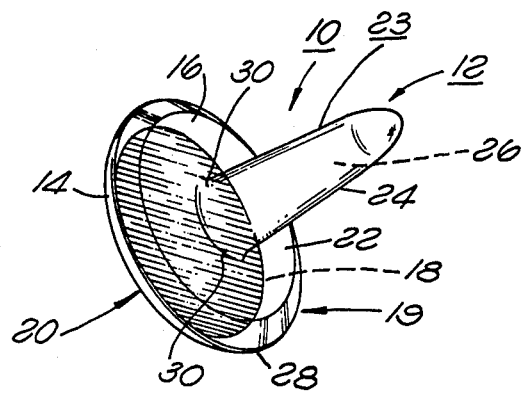
FIG. 1 is a perspective view of a preferred embodiment of a pressure detection arrangement according to the principles of the present invention.
Figure 2:
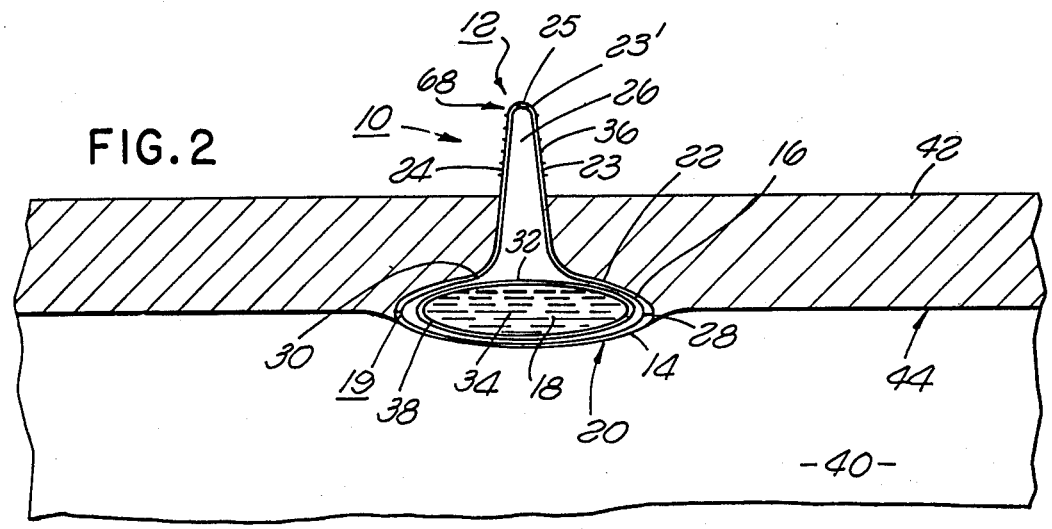
FIG. 2 is a sectional view of the embodiment of FIG. 1 as initially installed between a cast and a body portion.
Figure 3:
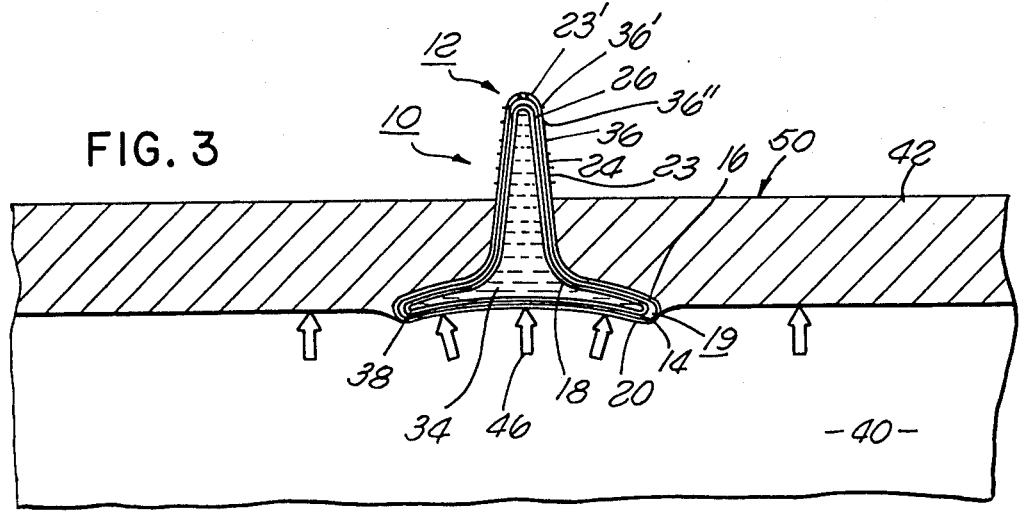
FIG. 3 is a sectional view similar to FIG. 2 showing the capsule subjected to pressure between the limb and the cast.

Referring now to the various figures of the drawings, there is illustrated in FIGS. 1, 2 and 3 an embodiment, generally designated 10 of a pressure detection arrangement of the present invention. Capsule 12 has a reservoir means 19 comprised of first walls 14 and second walls 16 defining a reservoir cavity 18. The first walls 14 further define a lower portion 20 of the reservoir cavity 18. First walls 14 are fabricated of a first material having a first predetermined flexibility. The second walls 16 further define an upper portion 22 of the reservoir cavity 18. The second walls 16 are fabricated of a second material having a second predetermined flexibility. An indicator means 23 is comprised of third walls 24 defining an indicator cavity 26. Third walls 24 are fabricated of a third material having a third predetermined flexibility. Third walls 24 may be either transparent or translucent.

First walls 14 are coupled to second walls 16 around the circumference of capsule 12 as shown at 28. Second walls 16 further define a first aperture 30 and third walls 24 are coupled to second walls 16 adjacent first aperture 30 to provide communication between indicator cavity 26 and reservoir cavity 18. The remote end 23' of indicator means 23 is closed. A separation means 32 which, in this embodiment comprises a flexible extensible bladder 38 is positioned within reservoir cavity 18 and contains an indicator fluid 34 which, under normal pressures, remains within reservoir cavity 18. The indicator means 23 may be provided with indicator marks 36 to assist in determining the pressure exerted on capsule 12.

The pressure detection arrangement of the present invention may advantageously be utilized in applications wherein a part of the body, such as a limb, is enclosed by other means comprising a structure such as a cast, a bandage wrapped around the body part, or the like. The description of the embodiments herein defines the utilization of the present invention in those applications wherein a cast is utilized around the body part. It will be appreciated that the present invention is not limited to only such applications and the use of a cast is selected for convenience of description.

Limb 40 is a body part that is the subject of the immobilization procedure requiring the application thereon of cast 42. One or more capsules 12 are placed on skin 44 with lower portion 20 touching skin 44. According to conventional procedures, the cast 42 is then built up around limb 40 and around capsule 12 in the normal manner. Capsule 12 thus becomes embedded in cast 42 as cast 42 is constructed.

FIG. 3 is a sectional view similar to FIG. 2 of embodiment 10 and illustrates the effect when pressure, as indicated by arrows 46, is exerted upon the flexible first walls 14 and second walls 16 of reservoir means 19. The reservoir cavity 18 is at least partially collapsed thereby forcing flexible extensible bladder 38 into indicator cavity 26. The examination of capsule 12 by a physician or the patient through transparent or translucent walls 24 reveals the presence of extensible bladder 38 filled with indicator fluid 34. The physician and the patient are thus alerted to the fact that excessive pressure exists and corrective action may be taken.

Indicator marks 36 may be utilized to indicate relative pressure within the limb 40. Extensible bladder 38, as represented, extends to a location between the first indicator mark 36' and second indicator mark 36''. After noting the position, the physician may decide to use drugs or other methods to reduce the pressure within the limb 40 without removing the cast 42. If a reduction in pressure is achieved, reservoir means 19 expands and extensible bladder 38 will retract into reservoir cavity 18, partially or totally. The effect of medication and other treatment can thus be read directly by comparing the location of extensible bladder 38 to indicator marks 36. If treatment utilizing medicines or other procedures does not reduce the pressure within the limb 40, removal of cast 42, or other procedures, can then be effectuated.

Figure 4:
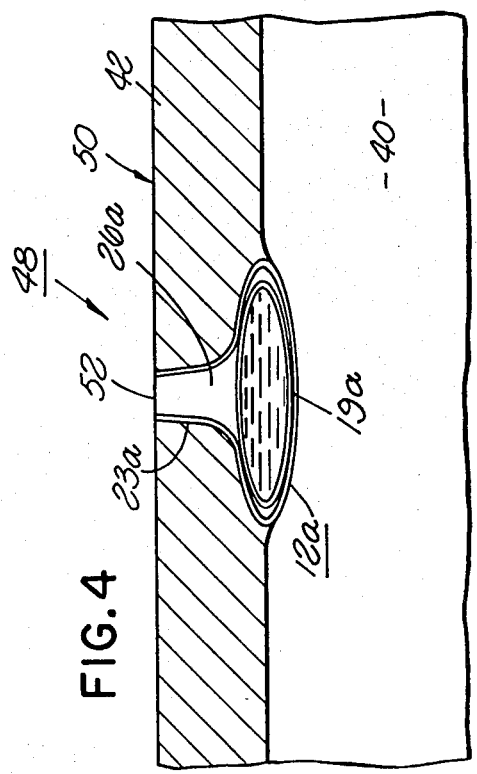
FIG. 4 is a sectional view similar to FIG. 2, of another embodiment of the present invention, having the indicator cavity trimmed flush with the outer surface of the cast.

FIG. 4 is a sectional view of another embodiment 48 of the present invention showing a capsule 12a having indicator means 23a trimmed flush with outer surface 50 of cast 42 to define a second aperture 52. Capsule 12a is generally similar to capsule 12 described above.

Figure 5:
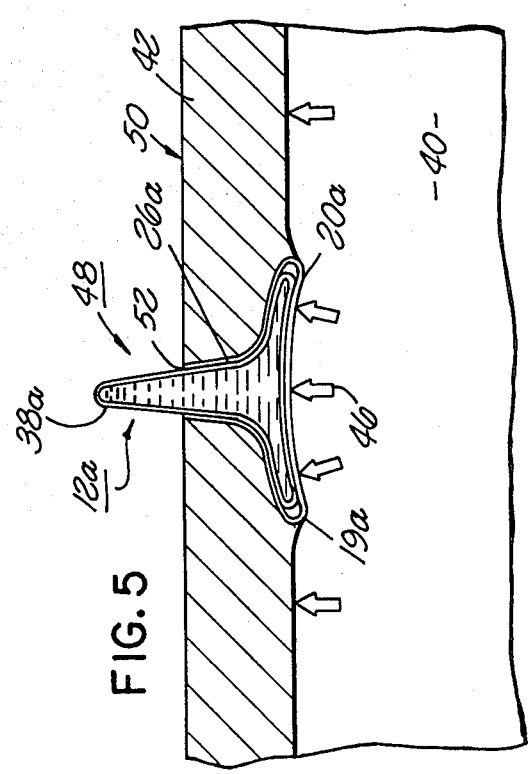
FIG. 5 is a sectional view similar to FIG. 4 showing the capsule subjected to pressure between the limb and the cast.

FIG. 5 is a sectional view of embodiment 48 of FIG. 4, similar to FIG. 3, after pressure indicated by arrows 46 is applied to capsule 12a. Extensible bladder 38a is thus forced up into indicator cavity 26a, through second aperture 52 and above outer surface 50 of cast 42. The appearance of extensible bladder 38a above outer surface of cast 42 indicates to a patient or physician that remedial steps are required.

In embodiment 10, a portion of indicator cavity 26 exists above outer surface 50 prior to any change in the location of extensible bladder 38. In embodiment 48 shown in FIGS. 4 and 5, however, extensible bladder 38a does not appear above outer surfaces 50 until pressure indicated by arrows 46 is applied to capsule 12a. Extensible bladder 38a thus provides both an improved visual and a tactual indication of excessive pressure within cast 42.

Figure 6:
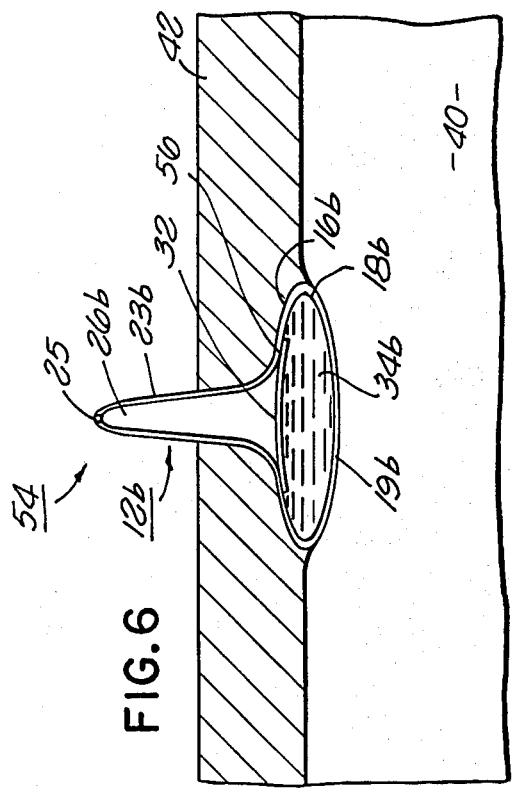
FIG. 6 is a sectional view similar to FIG. 2, of another embodiment of the present invention.

FIG. 6 is a sectional view similar to FIG. 2 of another embodiment 54 of the present invention in which a capsule 12b generally similar to capsule 12 is provided. In capsule 12b, however, there is a frangible disc 56 provided as the separation means 32. Frangible disc 56 is sealed, for example by bonding, heat sealing, or the like to the inside surface of second walls 16b of the reservoir means 19b of the capsule 12b to define the reservoir cavity 18b. Indicator fluid 34b is contained directly within reservoir cavity 18b without the use of a bladder such as is found in embodiments 10 of FIGS. 1, 2 and 3 and embodiment 48 of FIGS. 4 and 5. Thus, initially, in embodiment 54 the indicator cavity 26b of indicator means 23b is not in communication with the reservoir cavity 18b of reservoir means 19b.

When pressure, indicated by arrows 46, is applied to lower capsule 12b, frangible disc 56 is caused to rupture at a predetermined pressure. Indicator fluid 34b then passes through ruptured frangible disc 56 and out into indicator cavity 26b where it may be seen by the patient or physician.

Figure 8:
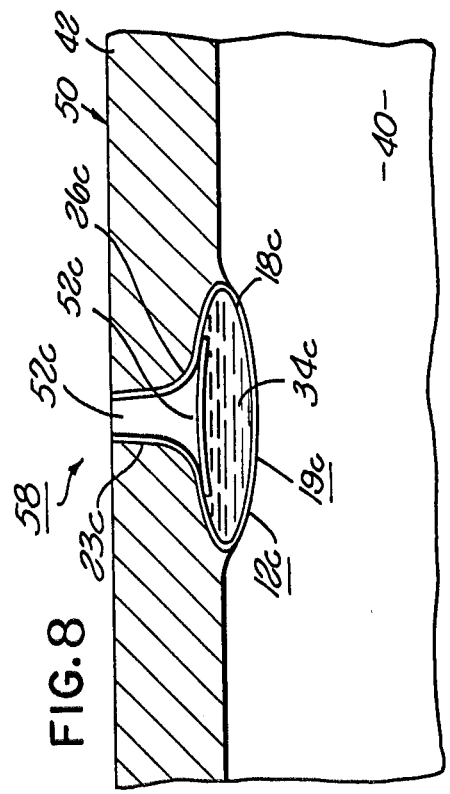
FIG. 8 is a sectional view similar to FIG. 6, of another embodiment of the present invention, having the indicator cavity trimmed flush with the outer surface of the cast.

FIG. 8 is a sectional view similar to FIG. 6 of another embodiment 58 of the present invention, having indicator cavity 26c of indicator means 23c of capsule 12c trimmed flush with outer surface 50 of cast 42. Frangible disc 56a retains indicator fluid 34c within reservoir cavity 18c 1 of reservoir means 19c.

Figure 9:
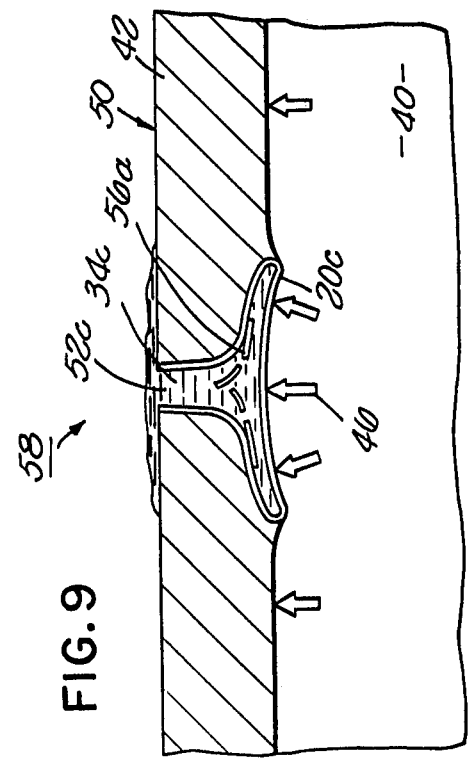
FIG. 9 is a sectional view similar to FIG. 8 showing pressure being exerted on the capsule causing the rupture of the frangible disc and the passage of the indicator fluid out of the indicator cavity and onto the outer surface of the cast.

FIG. 9 is a sectional view similar to FIG. 8 showing pressure indicated by arrows 46 being exerted upon capsule 12c. Frangible disc 56a has ruptured at a predetermined pressure thereby allowing indicator fluid 34c to enter indicator cavity 26c and flow out of second aperture 52c onto outer surface 50 of cast 42. Indicator fluid 34c thereby causes a mark on outer surface 50 of cast 42 and/or on other clothing or materials adjacent to the cast. The detection of pressure indicated by arrows 46 is thus readily apparent to either the patient or the physician.

It will be appreciated that, in another embodiment 57 of the present invention, a frangible bladder may also be used. In such an embodiment, the thickness and material of the bladder, such as bladder 38 of FIGS. 1, 2 and 3, are selected so that the bladder ruptures at a predetermined pressure. Alternatively, as shown in FIG. 13, an intentionally weakened portion 38b' of bladder 38b is provided to rupture at a predetermined pressure. The bladder 38b is within the reservoir cavity 18f of a reservoir means 19f of capsule 12f. Upon subjection to the predetermined pressure, the bladder 38b ruptures at 38b' allowing fluid 34f to pass into indicator cavity 26f of indicator means 23f.

Figure 7:
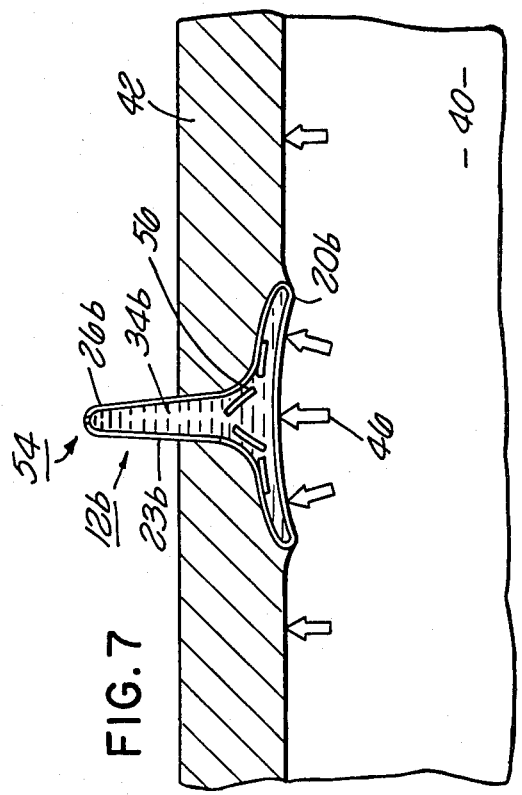
FIG. 7 is a sectional view similar to FIG. 6 showing pressure exerted between the limb and the cast upon the capsule.
Figure 10:
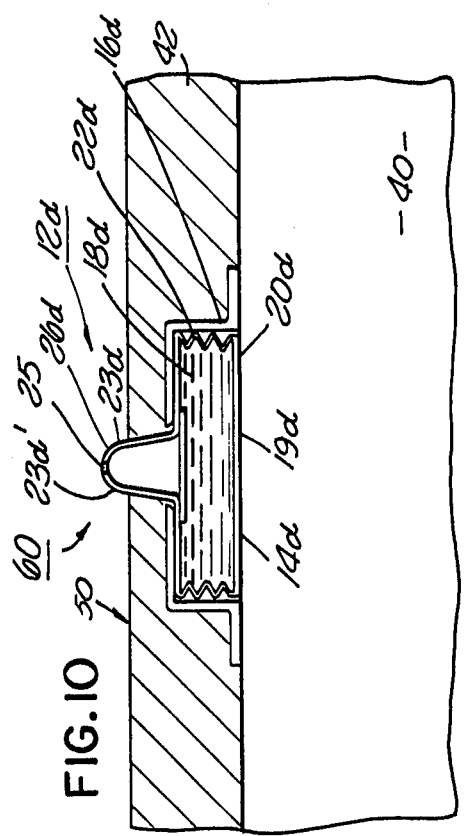
FIG. 10 is a sectional view of another embodiment of the present invention.

FIG. 10 is a sectional view of another embodiment 60 of the present invention. In all of the previous embodiments including 10 of FIGS. 2 and 3, 48 of FIGS. 4 and 5, 54 of FIGS. 6 and 7, and 58 of FIGS. 8 and 9, lower portion 20 of capsule 12 has first walls 14 which are flexurally collapsible into reservoir cavity 18. Upper portion 22 comprised of second walls 16 may also be partially flexurally collapsible into reservoir cavity 18. Embodiment 60 of FIG. 10, however, has a capsule 12d having a reservoir means 19d with a lower portion 20d thereof comprised of first walls 14d which remain substantially rigid. A decrease in the volume of reservoir cavity 18d is achieved by the flexural collapse of upper portion 22d comprised of second walls 16d. Capsule 12d is retained within a rigid cup 62. Capsule 12d has a frangible disc 56b initially separating indicator cavity 26d of indicator means 23d from reservoir cavity 18d.

Figure 11:
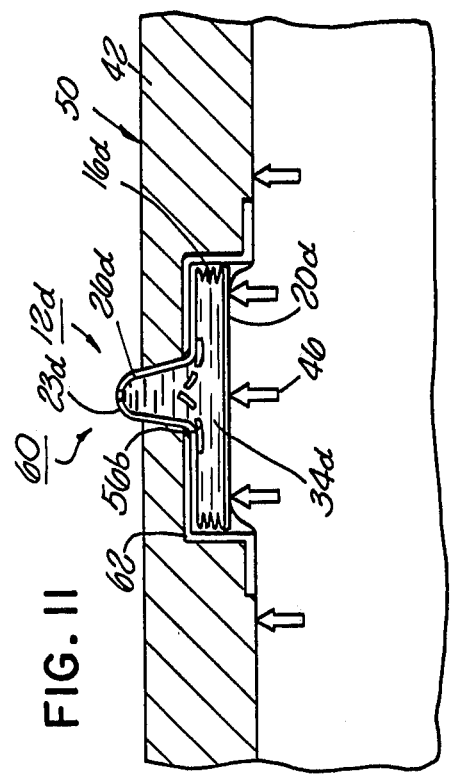
FIG. 11 is a sectional view similar to FIG. 10 showing the capsule under pressure.

FIG. 11 is a sectional view similar to FIG. 10 showing capsule 12d under pressure as indicated by arrows 46 on lower portion 20d. Pressure indicated by arrows 46 has forced lower portion 20d up into cup 62 collapsing a portion of second walls 16d and rupturing frangible disc 56b. Indicator fluid 34d has passed through frangible disc 56b into indicator cavity 26d thereby providing visual evidence of the pressure indicated by arrows 46 being exerted below.

It will be appreciated that rigid cup 62 of embodiment 60 of FIGS. 10 and 11 may also advantageously be utilized in other embodiments of the present invention. Thus, capsule 12 of FIGS. 1, 2 and 3, capsule 12a of FIGS. 4 and 5, capsule 12b of FIGS. 6 and 7, capsule 12c of FIGS. 8 and 9 and capsule 12f of FIG. 13 may also be installed in a rigid cup such as a rigid cup 62 when utilized.

The rigid cup, of course, provides the advantage, as may be desired in some applications, of insuring that the capsule is not subjected to initial pressurization when the cast is installed or is subjected only to a minimal initial pressurization.

In certain applications it may be desirable to have no portion of the capsule projecting above the outer surface of the cast and still provide that the outer end of the indicator means is closed. Further, it will be appreciated the thickness of the cast actually applied may vary not only in any one cast but also from cast to cast.

FIG. 12 illustrates an embodiment 64 of a capsule 12e which may be generally similar to any of capsules 12, 12a, 12b, 12c, 12d, and 12f except that the indicator means 23e thereof is initially fabricated with an elongated longitudinal dimension indicated at "l." The length "l" may be as long as desired and, preferably is greater than the thickness of the cast 42 placed upon the limb 40. The indicator means 23e has third walls 24e defining the indicator cavity 26e. The capsule 12e may, if desired, be positioned within a rigid cup 62.

After the cast 42 is placed on the limb 40, the outer portion 23e' of indicator means 23e which extends beyond the outer surface 50 of cast 42 may be removed by serving along the line 66 at the outer surface 50 of cast 42 and discarded. A transparent or translucent cap means 68 is then installed in the indicator cavity 26e preferably with its outer surface 70 flush with the surface 50. The rise of the indicator fluid into the portion 26e' of indicator cavity 26e is then visible through the cap 68.

In other applications, it may be desirable to provide a small vent hole 25 in the outer tip, such as outer tip 23' of FIGS. 2 and 3, to allow outflow of the air in the indicator cavity 26 as the bladder 38 extends therein. This reduces the pressure level necessary to cause a predetermined rise of the bladder 38. Similarly, vent holes may also be provided in the outer tip 23b' of FIGS. 6 and 7 or 23d of FIGS. 10 and 11 for the same purpose as the indicator fluid 34b or 34d rises in the indicator cavity 26b or 26d, respectively.

This concludes the description of the preferred embodiments of the present invention. Those skilled in the art may find many variations and adaptations thereof and the attached claims are intended to cover all such variations and adaptations falling within the true scope and spirit of the invention.

What is claimed is:

1. A pressure detection arrangement for placement intermediate a part of the body means surrounding the part of the body and comprising, in combination:
   capsule comprising:
      a reservoir means having first walls and second walls defining a reservoir cavity, and said first walls further defining a lower portion of said reservoir cavity having a first predetermined flexibility, and said second walls further defining an upper portion of said reservoir cavity having a second predetermined flexibility;
      an indicator means having third walls defining an indicator cavity having a third predetermined flexibility and having a preselected transmissivity for electromagnetic radiation in the visible portion of the electromagnetic radiation spectrum to allow visual inspection therethrough of said indicator cavity;
      said first walls coupled to said second walls;
      said second walls further defining a first aperture through said second walls;
      said third walls coupled to said second walls adjacent said first aperture; and
      a separation means comprising a frangible disc across said first aperture to close communication between said reservoir cavity and said indicator cavity; and
      an indicator fluid in said reservoir cavity said separation means responsive to a predetermined pressure exerted on said indicator fluid in said reservoir cavity to fracture said frangible member to allow said indicator fluid to enter said indicator cavity and said separation means separating said indicator fluid from said third walls of said indicator means for the condition of said reservoir cavity subjected to less than said predetermined pressure.

2. A pressure detection arrangement for placement intermediate a part of the body and means surrounding the part of the body and comprising, in combination:
   a capsule comprising:
      a reservoir means having first walls and second walls defining a reservoir cavity, and said first walls further defining a lower portion of said reservoir cavity having a first predetermined flexibility, and said second walls further defining an upper portion of said reservoir cavity having a second predetermined flexibility;
      an indicator means having third walls defining an indicator cavity having a third predetermined flexibility and having a preselected transmissivity for electromagnetic radiation in the visible portion of the electromagnetic radiation spectrum to allow visual inspection therethrough of said indicator cavity;
      said first walls coupled to said second walls;
      said second walls further defining a first aperture through said second walls;
      said third walls coupled to said second walls adjacent said first aperture; and
      a separation means across said first aperture to close communication between said reservoir cavity and said indicator cavity, and said separation means comprising a frangible bladder within said reservoir cavity; and
      an indicator fluid in said frangible bladder said separation means responsive to a predetermined pressure exerted on said indicator fluid in said reservoir cavity to fracture said frangible member to allow said indicator fluid to enter said indicator cavity and said separation means separating said indicator fluid from said third walls of said indicator means for the condition of said reservoir cavity subjected to less than said predetermined pressure.

3. A pressure detection arrangement for placement intermediate a part of the body and means surrounding the part of the body and comprising, in combination:
a capsule comprising:
a reservoir means having first walls and second walls defining a reservoir cavity, and said first walls further defining a lower portion of said reservoir cavity having a first predetermined flexibility, and said second walls further defining an upper portion of said reservoir cavity having a second predetermined flexibility, and said first or said second walls flexurally collapsible into said reservoir cavity;
an indicator means having third walls defining an indicator cavity having a third predetermined flexibility and is transparent and having a preselected transmissivity for electromagnetic radiation in the visible portion of the electromagnetic radiation spectrum to allow visual inspection therethrough of said indicator cavity, and said third walls closed at the end of said indicator cavity spaced from said reservoir cavity, and said third walls further comprise indicator marks;
said first walls coupled to said second walls;
said second walls further defining a first aperture through said second walls;
said third walls coupled to said second walls adjacent said first aperture; and
a separation means comprising a frangible disc across said first aperture to close communication between said reservoir cavity and said indicator cavity; and
a radiographic indicator fluid in said reservoir cavity said separation means responsive to a predetermined pressure exerted on said indicator fluid in said reservoir cavity to fracture said frangible member to allow said indicator fluid to enter said indicator cavity and said separation means separating said indicator fluid from said third walls of said indicator means for the condition of said reservoir cavity subjected to less than said predetermined pressure.

4. A pressure detection arrangement for placement intermediate a part of the body and means surrounding the part of the body and comprising, in combination:
a capsule comprising:
a reservoir means having first walls and second walls defining a reservoir cavity, and said first walls further defining a lower portion of said reservoir cavity having a first predetermined flexibility, and said second walls further defining an upper portion of said reservoir cavity having a second predetermined flexibility, and said second walls flexurally collapsible into said reservoir cavity;
a rigid cup surrounding said upper portion of said reservoir cavity;
an indicator means having third walls defining an indicator cavity having a third predetermined flexibility and having a preselected transmissivity for electromagnetic radiation in the visible portion of the electromagnetic radiation spectrum to allow visual inspection therethrough of said indicator cavity, and said third walls further define a second aperture spaced from said reservoir cavity;
said first walls coupled to said second walls;
said second walls further defining a first aperture through said second walls;
said third walls coupled to said second walls adjacent said first aperture; and
a separation means across said first aperture to close communication between said reservoir cavity and said indicator cavity;
an indicator fluid in said reservoir cavity; and a cap means fabricated of one of a translucent and a transparent material and inserted in and closing said second aperture.

* * * * *